June 25, 1974 W. A. WARRINER Plant Pat. 3,579
ROSE PLANT
Filed Jan. 8, 1973
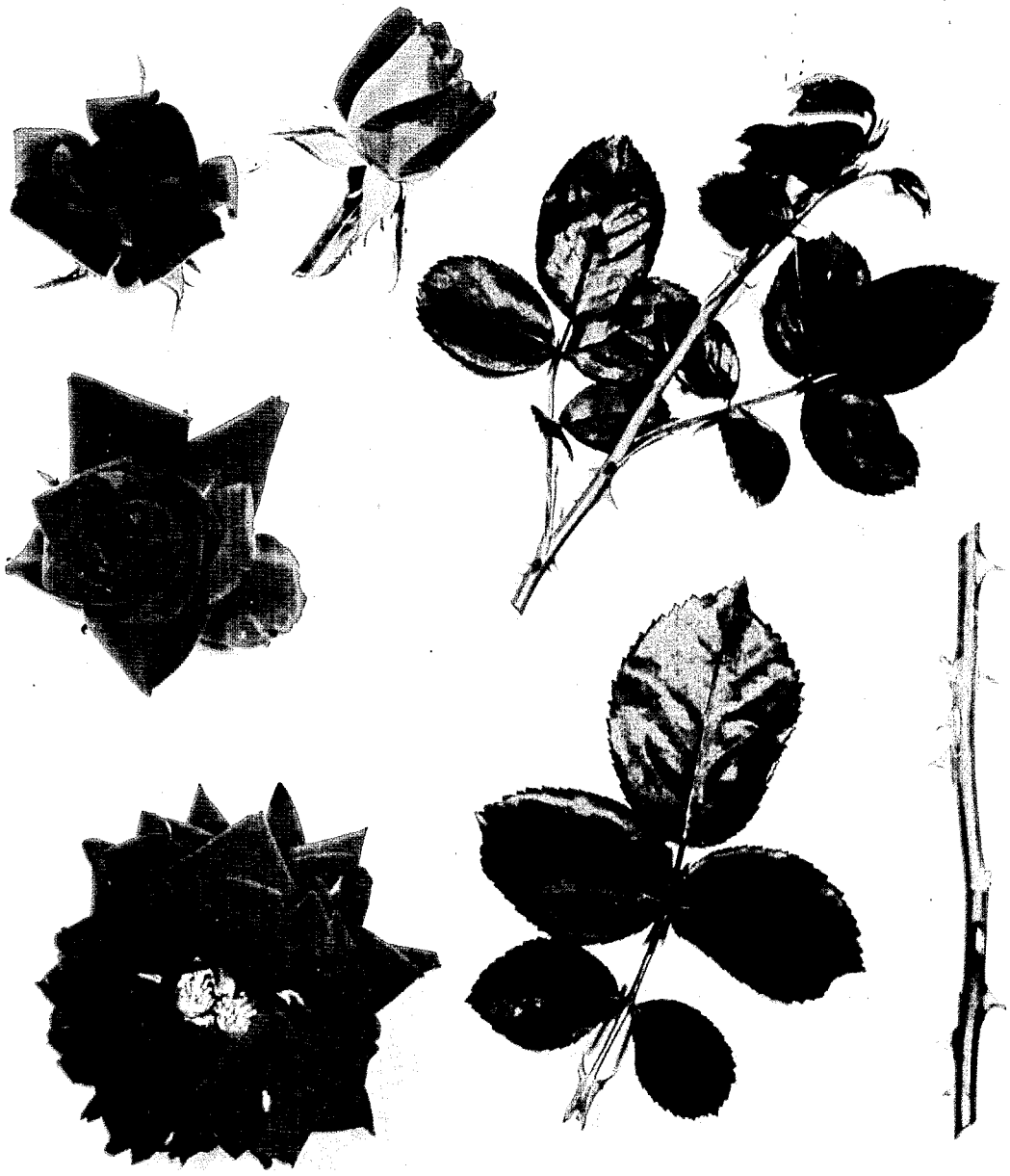

United States Patent Office

Plant Pat. 3,579
Patented June 25, 1974

3,579
ROSE PLANT

William A. Warriner, Tustin, Calif., assignor to Jackson & Perkins Company, Medford, Oreg.

Filed Jan. 8, 1973, Ser. No. 321,815
Int. Cl. A01h 5/00
U.S. Cl. Plt.—21 1 Claim This present invention relates to a new and distinct variety of rose plant in a class intermediate between hybrid tea and floribunda which was originated by me by crossing two unnamed, undistributed rose varieties.

The primary objective of this breeding was to produce a new rose variety, taller than the floribunda class but with the usual large number of flowers produced by plants of the floribunda class. This objective was substantially achieved along with other desirable improvements as evidenecd by the following unique combination of characteristics which are outstanding in the variety and which distinguish it from its parents as well as from all other varieties of which I am aware:

1. A unique habit of growth, producing many flowers on long stems in clusters.
2. An extremely high resistance to rose powdery mildew.
3. An overall flower color close to Wilson's Cardinal Red which is fast in all seasons.
4. Dark, semi-glossy foliage.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with *Wilsons Horticultural Color Chart*, except where ordinary dictionary significance of color is indicated.

Parentage: Seedling.
*Seed parent.*—Unnamed variety.
*Pollen parent.*—Unnamed variety.
Classification:
*Botanic.*—Rosa hybrid.
*Commercial.*—Intermediate between hybrid tea and floribunda.

FLOWER

Observations were made at Irvine, Calif., in mid-October in the afternoon of plants and blooms from the garden.

Blooming habit: Recurrent—continuous.
Bud:
*Size.*—¾ inch when petals start to unfurl.
*Form.*—Ovoid.
*Color.*—When sepals first divide, near Chrysanthemum Crimson (824). When half blown; inside of petals, near Cardinal Red (822). Reverse of petals, near Cardinal Red (822/3).
*Sepals.*—Color: Outer surface—Scheeles Green (860/3). Inner surface—slightly darker than outside but covered with white tomentum. Three appendaged sepals lightly appendaged. Two unappendaged sepals smooth edged.
*Receptacle.*—Color: Scheeles Green (860/3). Shape: Funnel. Size: Large. Surface: Smooth.
*Peduncle.*—Length: Medium. Surface: Prickly. Color: Light green. Strength: Stiff, erect.
*Opening.*—Slightly incurved petals fold out, then outer petals quill slightly—center petals quill very little.

Bloom:
*Size.*—Medium. Average size when fully expanded, 3 inches.
*Borne.*—Singly and in clusters—rounded. Individual flowers in clusters on long stems.
*Stems.*—Long, strong.
*Form.*—When first open, high center. Permanence—retains its form until the end.
*Petalage.*—Number of petals under normal conditions, 40.
*Color.*—Center of flower: Upper side of petals near Cardinal Red (822). Reverse side of petals slightly lighter than Cardinal Red (822/3). Outer petals: Upper side of petals same as center petals. Base of petals: Sharply defined rectangular area of Empire Yellow (603). General tonality from a distance near Cardinal Red (822).
*Discoloration.*—By third day, exposed surface slightly darker, covered petal surface slightly lighter; yellow base lightens to near white.
*Fragrance.*—None.
Petals:
*Texture.*—Thick.
*Surface.*—Inside—shiny. Reverse—satiny.
*Shape.*—Round.
*Form.*—Moderately quilled.
*Arrangement.*—Irregular.
*Petaloids in center.*—Few, large.
*Lastingness.*—On the plant—very long. As cut flower—very long.
Reproductive parts:
*Stamens, anthers.*—Large. Color—yellow. Arrangement—regular around styles.
*Stamens, Filaments (threads).*—Assorted. Color—yellow.
*Pollen.*—Lemon yellow.
*Styles.*—Loosely separated, of uneven lengths. Thin.
*Stigmas.*—Color—white.

PLANT

Form: Bush.
Growth: Very vigorous, upright, branching.
Foliage: Number of leaflets on normal mid-stem leaves, 5 sometimes 7.
*Size.*—Medium.
*Quantity.*—Normal.
*Color.*—New foliage: Garnet Brown (00918/3). Old foliage: Near Parsley Green (00962), upper side. Little lighter than Spinach Green (0960/3), lower side.
Leaflets:
*Shape.*—Oval pointed.
*Texture.*—Upper side semi-glossy.
*Edge.*—Serrated.
*Serration.*—Single, small.
*Petiole (rachis).*—Color — Green. Underside—prickles. Upperside—numerous stipitate glands.
*Stipules.*—Long, mostly adnate with stipitate glands.
*Disease resistance.*—Resistant to mildew under normal growing conditions at Irvine, Calif.
Wood:
*New wood.*—Color—light green. Bark—smooth.
*Old wood.*—Color—green. Bark—smooth.
Prickles:
*Quantity.*—On main stalks—many. On laterals—many.
*Form.*—Broad base, long, hooked downward.
*Color.* — When young — near Garnet Brown (00918/3).

Small Prickles:

*Quantity.*—On main stalks—many. On laterals—many.

*Color.*—Brown.

The plant branches freely from base and makes many long stem clusters of blooms.

I claim:

1. A new and distinct variety of rose plant of a class between hybrid tea and floribunda, substantially as herein shown and described, characterized particularly as to novelty by the unique combination of Cardinal Red flowers borne in clusters on an upright plant of hybrid tea size; very high resistance to rose powdery mildew; and its dark green, semi-glossy foliage.

No references cited.

ROBERT E. BAGWILL, Primary Examiner